(12) United States Patent
Cohen

(10) Patent No.: US 8,227,637 B2
(45) Date of Patent: Jul. 24, 2012

(54) STABLE, WATER-SOLUBLE NEAR INFRARED DYES

(75) Inventor: Murray S. Cohen, Morristown, NJ (US)

(73) Assignee: Epolin, Inc., Newark, NJ (US)

( * ) Notice: Subject to any disclaimer, the term of this patent is extended or adjusted under 35 U.S.C. 154(b) by 997 days.

(21) Appl. No.: 12/051,238

(22) Filed: Mar. 19, 2008

(65) Prior Publication Data

US 2009/0236571 A1    Sep. 24, 2009

(51) Int. Cl.
*C07C 229/34* (2006.01)
(52) U.S. Cl. ........................................ 562/457
(58) Field of Classification Search .............. 562/457
See application file for complete search history.

(56) References Cited

U.S. PATENT DOCUMENTS

| | | | |
|---|---|---|---|
| 3,341,464 A | 9/1967 | Susi et al. ............... 252/300 |
| 3,400,156 A | 9/1968 | Milionis et al. ............... 564/8 |
| 3,440,257 A | 4/1969 | Susi et al. ............... 260/440 |
| 3,484,467 A | 12/1969 | Susi et al. ............... 260/440 |
| 3,575,871 A | 4/1971 | Susi et al. ............... 252/300 |
| 3,631,147 A | 12/1971 | Susi ............... 260/45.75 |
| 3,637,769 A | 1/1972 | Susi ............... 260/396 |
| 3,670,025 A | 6/1972 | Susi et al. ............... 260/576 |
| 3,709,830 A | 1/1973 | Susi ............... 252/300 |
| 3,962,290 A | 6/1976 | Grosso ............... 552/301 |
| 5,605,732 A | 2/1997 | Mihara et al. ............... 428/64.8 |
| 5,686,639 A | 11/1997 | Cohen ............... 556/33 |
| 6,210,849 B1 | 4/2001 | Fukuda et al. ............... 430/106 |
| 2006/0199105 A1 | 9/2006 | Cahill ............... 430/270.11 |

FOREIGN PATENT DOCUMENTS

| | | | |
|---|---|---|---|
| JP | 7-133475 | * | 5/1995 |
| JP | 7-144475 | * | 5/1995 |

OTHER PUBLICATIONS

Song et al. (Dyes and Pigments 78 (2008) 60-64).*
STN Abstract of Mihara et al., JP (1995) 7-144475.*
MAchine translation of Mihara et al., JP (1995) 7-144475.*
Hebden (J. Indust. Eng. Chem., v. X (1918), n. 8, p. 640-44).*
STN Abstract of Mihara et al., JP (1995) 7-133475.*
MAchine translation of Mihara et al., JP (1995) 7-133475.*
Dabbagh et al. (Dyes and Pigments 54 (2002) 37-46).*

* cited by examiner

*Primary Examiner* — Robert Havlin
(74) *Attorney, Agent, or Firm* — Roberts & Roberts, LLP

(57) ABSTRACT

The synthesis of stable, water-soluble tris and tetrakis aminium dyes. More particularly, carboxylic-acid modified tris and tetrakis dye intermediates, as well as salts and near-infrared dyes formed therefrom, as well as compositions including the dyes.

6 Claims, No Drawings

STABLE, WATER-SOLUBLE NEAR INFRARED DYES

BACKGROUND OF THE INVENTION

1. Field of the Invention

The invention relates to the synthesis of tris and tetrakis aminium dyes. More particularly, the invention pertains to aminium dye precursors, as well as salts and near infrared (IR) dyes formed therefrom.

2. Description of the Related Art

Near IR dyes are well known in the art. The spectral properties of infrared light absorbing aminium dyes was first reported by Otto Neunhoeffer and Peter Heitmann (see Neunhoeffer et al., *Chemische Berichte* 92, 245-251 (1959) and Neunhoeffer et al., *Chemische Berichte* 94, 2511-2515 (1961)). Subsequent development of these dyes at the American Cyanamid Company of Stamford, Conn. by Peter Susi and colleagues is reported in U.S. Pat. Nos. 3,341,464, 3,440,257, 3,484,467, 3,575,871, 3,631,147, 3,637,769, 3,670,025 and 3,709,830 to Susi et. al., as well as U.S. Pat. No. 3,400,156 (Milionis et al.), U.S. Pat. No. 3,962,290 (Grosso) and U.S. Pat. No. 5,686,639 (Cohen et al.), the disclosures of which are incorporated herein by reference. Various other patents disclose methods of preparation of intermediates and the use of such aminium salts as near infrared dyes.

In general these dyes have the property of passing light in the visible portion of the spectrum (450 to 700 nanometers) and absorbing strongly in the near IR portion of the spectrum (900 to 1300 nanometers). By their use, it is possible to sequester about 35 to 50 percent of the sun's total energy. The amount is much higher when absorbing radiation from tungsten filament lamps. These dyes can be incorporated in a variety of plastics and can be used as sunglasses, welding shields, laser protection eyewear, windows, television filters, projection lenses and other products which can attenuate the heat from radiant sources or absorb specific laser radiation. As described in the referenced patents, the dye is incorporated into plastic film or sheet by molding the plastic with the dye, imbibing the dye into the preformed plastic sheet or by forming the sheet by cell casting and polymerizing the polymerizable monomer containing the dissolved dye.

Near infrared dyes are commonly synthesized from tris and tetrakis amines. These intermediates are converted into salts and oxidized to form dyes. For example, U.S. Pat. No. 3,709,830 provides p-Quinonediimonium salts and their use as infrared absorbers. This patent discloses the synthesis of N,N',N'',N'''-tetrakis(4-[di(2-hydroxyethyl)amino]-phenyl)-p-benzoquinonebis(imonium hexafluoro-antimonate) by combining N,N',N'',N'''-tetrakis(4-[di(2-hydroxyethyl)amino]phenyl)-p-phenylenediamine with methanol and silver hexafluoroantimonate. This $SbF_6$ salt is not water-soluble and other salts have minimal water solubility. The present invention provides a new class of water-soluble, near infrared dyes that are obtained by the oxidation of carboxylic acid-modified tris or tetrakis amines. These dyes allow a similar maximization of the frequency range of absorption while at the same time allowing transmission in the visible range to be as transparent as possible. Further, one particular advantage offered by these water-soluble dyes is their very high solubility in mixed aqueous coating systems. These coatings are very thin (approx 0.5 mil to 1.0 mils). For example, if the concentration of dye used in an 80 mil optical lens requires 0.1 to 0.5% of near infrared dye, then a thin coating would need a concentration of dye 50-100 times as great, and approximately 4% by weight of dye in the dry coating weight would be used in such a coating. Accordingly, the present invention provides a solution to the existing needs in the art.

SUMMARY OF THE INVENTION

The invention provides a compound of the formula:

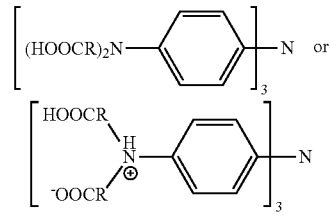

where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$.

The invention also provides a process for producing a carboxyl-modified compound, comprising reacting a tris amine of the formula:

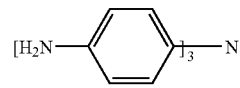

with an alkenyl-substituted carboxylic acid of the formula RCOOH, where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$, to produce a carboxyl-modified compound of the formula:

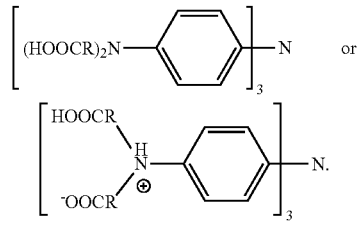

The invention further provides a compound of the formula:

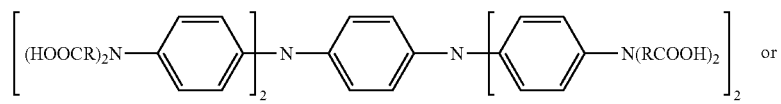

-continued

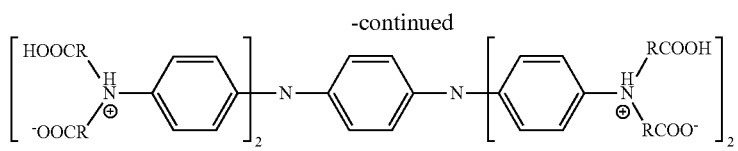

where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$.

The invention also provides a process for producing a carboxyl-modified compound, comprising reacting a tetrakis amine of the formula:

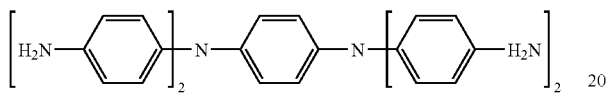

with an alkenyl-substituted carboxylic acid of the formula RCOOH, where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$, to produce a carboxyl-modified compound of the formula:

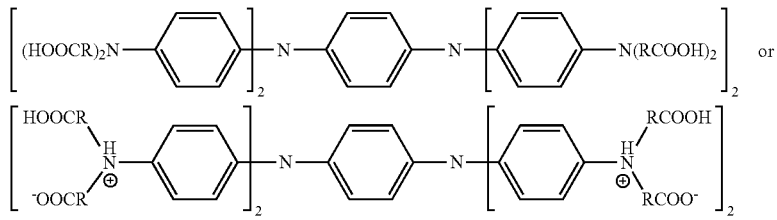 or

DESCRIPTION OF THE INVENTION

The stable, water-soluble near infrared dyes of the invention are synthesized from either tris or tetrakis amine starting materials. Such tris amine starting materials have the formula:

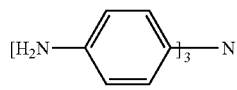

Such tetrakis amine starting materials have the formula:

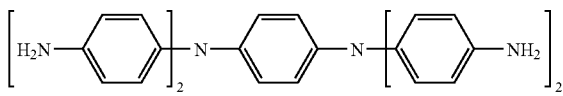

With regard to tris dyes, a tris amine is modified by reaction with an alkenyl-substituted carboxylic acid of the formula RCOOH, where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$, to form a carboxyl-modified compound:

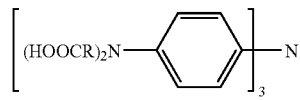

where $R^3$ will bond to nitrogen. Suitable carboxylic acid monomers non-exclusively include unsaturated aliphatic monocarboxylic acids such as acrylic acid, methacrylic acid, crotonic acid and oleic acid. Of these, acrylic acid is most preferred, producing a tris di-2-carboxyethylaminophenyl amine compound of the formula:

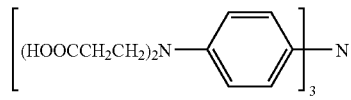

Typically, the reaction is conducted by allowing the tris amine to react with an excess of the carboxylic acid. The reaction temperatures are ordinarily from about 20° C. to about 70° C., with 60° C. most preferred. The reaction is typically conducted for about 1 to about 3 hours and may be catalyzed by acrylic acid itself, acetic acid and/or other aliphatic carboxylic acids in amounts up to equimolar which is typically added prior to the addition of the unsaturated carboxylic acid. The product may be recovered by the addition of about 5 to about 10 volumes of water, allowing solids to precipitate which are separated by filtration and washed with water and air dried.

The carboxyl-modified compound is subsequently reacted with a base such as compounds $R^1$-OH, $R^1_2CO_3$ or $R^1HCO_3$, which forms a salt having the formula:

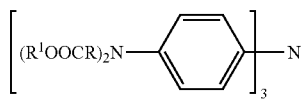

wherein $R^1$=$Na^+$, $K^+$, $Ca^{++}$, $(CH_3)_4N^+$, $NH_4^+$, $(CH_3)_3NH^+$, $(R^2)_3NH^+$ or $R^2NH_2^+$ and $R^2$=$CH_3(CH_2)_n$, wherein n=2 to 10. An example of a salt produced from reaction with $(R^2)_3NH^+$ is the formula:

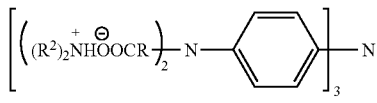

Weak bases, such as $NH_3$, $(CH_3)_3N$, $NaHCO_3$ and $CaCO_3$, may also be used, and these may also be defined as a compound $R^1OH$ because $NH_3$ exists as $NH_4^+OH^-$, $(CH_3)_3N$ as $(CH_3)_3NH^+OH^-$, $NaHCO_3$ as $Na^+\ OH^-+CO_2$, and $CaCO_3$ as $Ca^{++}(OH^-)_2+2CO_2$. Other amines, such as $NH_4^+OH^-$ and $R_3NH^+OH^-$, etc., may also be used as compound $R^1OH$. The reaction with the carboxylic acid group thereby gives a salt as though derived from $R^1OH$.

When R above comprises an ethyl group, as is preferred, the salt has the formula:

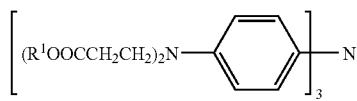

The salt formation with $R^1OH$ depends upon the strength of the base used. When a strong base is used, such as NaOH, KOH, $Ca(OH)_2$, tetramethylammonium hydroxide or other quaternary ammonium hydroxides, the carboxylic acid is almost completely neutralized, achieving complete replacement of the acid hydrogen of all the carboxylic acid groups. When a weak base is used, such as $NH_3$, $NaHCO_3$ or $(CH_3)_3N$, the ratio of free —COOH groups to weak base salts varies with the base strength due to competition with zwitterion formation. For example, when R is an ethyl group and an $NH_4^+OH^-$ base is utilized, a zwitterion may be formed having the formula:

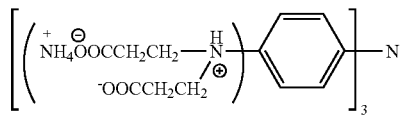

With the strong bases, the stoichiometry approaches about 1 mole of base for each —COOH group. When a weak base is used, the ratio of base to —COOH is less than equimolar. The reaction temperatures used in the salt formation reactions are not critical. Ordinarily, temperatures from about 20° C. to about 50° C. are used.

Most preferably, the carboxyl-modified compound is reacted with a strong base, such as NaOH. However, because the —N group is a base and the —COOH group is an acid, in aqueous solution, an $H^+$ ion may be transferred from the carboxylic acid group to the basic amine to form a zwitterion (hybrid ion), having the formula:

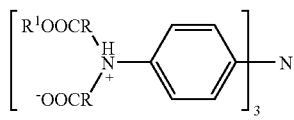

or when R comprises a dimethylene group, the zwitterion has the formula:

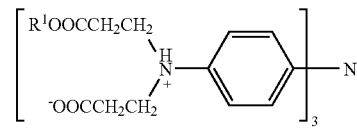

The zwitterion is simultaneously electrically charged and electrically neutral as it contains equal positive and negative charges, so that the net charge on the molecule is zero. This typically occurs due to reaction with a weak base, such as $NaHCO_3$, $NH_3$, $R_3N$ and other amines, such as $NH_4^+OH^-$, $R_3NH^+OH^-$, etc. The reaction with any one of the bases, both organic and inorganic, will give a zwitterion corresponding to the degree of basicity of the base. Thus, $NaHCO_3$, and organic amines will have similar but somewhat different isoelectric points (degree of internal salt formation) than that of strong bases such as NaOH, KOH or even $CaCO_3$ and $K_2CO_3$. Even these to some small extent may not go all the way to the corresponding salt. Zwitterions also can form when there is a free —COOH group and an amine in close proximity.

After formation of the salt, the dyes of the invention are formed by oxidation of this salt with an oxidant. Suitable oxidants non-exclusively include copper salts such as cupric chloride, cupric bromide, cupric sulfate and acetate, as well as silver salts including silver nitrate ($AgNO_3$), silver acetate ($AgC_2H_3O_2$), silver hexafluoroantimonate ($AgSbF_6$) silver hexafluorophosphate ($AgPF_6$). Cupric chloride, cupric bromide, cupric sulfate and cupric nitrate are also used. Generally any cupric or silver salt which is soluble to an appreciable extent in a compatible organic solvent may be used in the oxidation reaction. Other useful oxidants include N-bromosuccinimide, $FeCl_3$ or a peroxide, particularly alkyl peroxides such as tert-butyl hydroperoxide or benzoyl peroxide. However, these give intermediates which are suitable as will be explained for substation with $NaSbF_6$, $NaPF_6$ or other salts of strong acids. Oxidation of the tris salt forms a dye having the formula:

(I)(A)

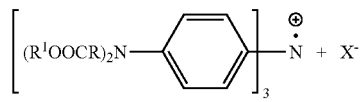

or the zwitterion:

(I)(B)

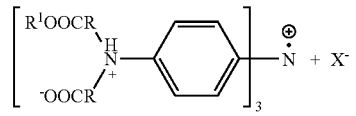

wherein X is preferably an anion of a strong acid and preferably comprises $NO_3^-$, $Cl^-$, $Br^-$, tetrafluoroborate ($BF_4^-$), hexafluorophosphate ($PF_6^-$) or hexafluoroantimonate ($SbF_6^-$). Most preferably, X comprises $NO_3^-$, $SbF_6^-$ or $PF_6^-$. All of the compounds represented by these formulas (I)(A),(B) (and formula (II)(A),(B) and II (C), (D) as shown below) are stable, water-soluble near IR dyes in that they absorb electromagnetic radiation in the range of 900 nanometers to 1300 nanometers. Any of the above compounds may be blended with most water-soluble polymers and/or stable aqueous latex formulations to form IR absorbing compositions.

The oxidation reaction is preferably carried out in a mixed aqueous-alcohol solvent in which the carboxyl-modified salt and the oxidant are at least partially soluble. The solvent used is not critical provided it is inert to the reactants and the product under the reaction conditions. Water and methanol are preferred solvents due to their ease of handling, however, other solvents, such as dimethylformamide, dimethylacetamide and tetrahydrofuran also give good results. The amount of the oxidant used in the oxidation reaction is about one mole per mole of the carboxyl-modified salt. The reaction temperatures used in the oxidation are not critical. Ordinarily, temperatures from about 20° C. to about 50° C. are used. Generally, following completion of the oxidation, any remaining oxidant is removed by filtering and the product is isolated from solution by precipitation with acetone. The product is then filtered off, washed free of solvent and dried, according to standard techniques.

This optional treatment can add a cation to the carboxylic acid, forming a neutrally charged species of the dye which is more stable and more easily isolated. However, in some cases the dye may be made from the carboxylic acid itself.

Similar reactions apply with regard to tetrakis dyes using similar procedures to prepare and isolate the tetrakis carboxylic acid as the tris product. A tetrakis amine is modified by reaction with an alkenyl-substituted carboxylic acid of the formula RCOOH, where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$, to form a carboxyl-modified compound:

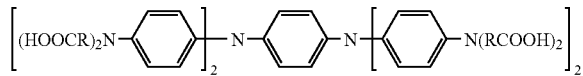

Suitable carboxylic acid monomers are those described previously for the tris dyes. Most preferably, the carboxylic acid is acrylic acid, producing a tetrakis-2-dicarboxyethylaminophenyl phenylene diamine compound of the formula:

The carboxyl-modified compound is subsequently reacted with a base compound such as $R^1$-OH, $R^1_2CO_3$ or $R^1HCO_3$ to form a salt having the formula:

Thereafter, the oxidized dye may be further treated by displacing the ion $X^-$ of the ionized dye compound with one or more counter-ions $Y^-$ to form another salt of the dye, having the formula:

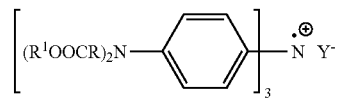

where Y is preferably $NO^-_3$, $SbF^-_6$, $BF^-_4$ or $PF^-_6$.

wherein $R^1$=$Na^+$, $K^+$, $Ca^{++}$, $(CH_3)_4N^+$, $NH_4^+$, $(CH_3)_3NH^+$, $(R^2)_3NH^+$ or $R^2NH_2^+$ and $R^2$=$CH_3(CH_2)_n$, wherein n=2 to 10. As described above, a compound $R^1$-OH includes weak bases, such as $NH_3$, $(CH_3)_3N$, $NaHCO_3$ and $CaCO_3$ and other amines, such as $NH^+_4OH^-$ and $R_3NH^+OH^-$, etc, where reaction with the carboxylic acid group gives a salt as though derived from $R^1OH$ as previously mentioned.

The general conditions described for the tris compounds are applicable to the preparation of carboxylate salts of the tetrakis products.

When R comprises an ethyl group, the salt has the formula:

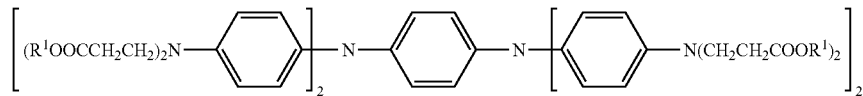

To effect this replacement of anions, the dye that is formed, usually as a nitrate salt, is dissolved in methanol and treated with an excess of a salt of the substituted counter ion. In the case of $NaSbF_6$, such treatment results in the precipitation of sodium nitrate which is removed from the reaction mixture by filtration. The product containing the substituted anion, is precipitated by the addition of acetone.

Most preferably, the carboxyl-modified compound is reacted with a strong base, whereas a weak base may form a zwitterion having the formula:

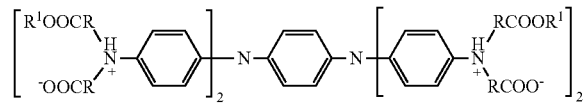

or when R comprises an ethyl group, the zwitterion has the formula:

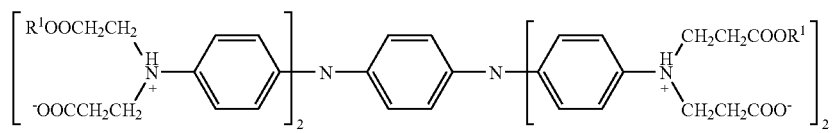

After formation of the salt, the dyes of the invention are formed by oxidation of this salt with an oxidant. Suitable oxidants and oxidation conditions are the same as described above for the tris dyes. However, oxidation of the tetrakis salt can form two dyes having the formulas (II)(A) and (II)(B), and II(C) and II(D), to represent the mono and dioxidized dyes:

The monovalent dye salt:

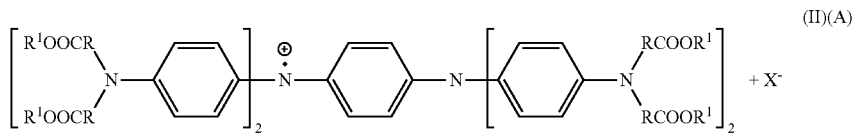

or the zwitterion:

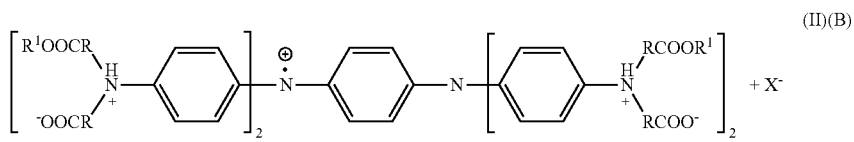

For the divalent dye salt:

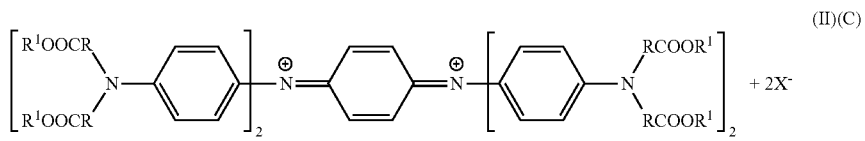

or the zwitterion:

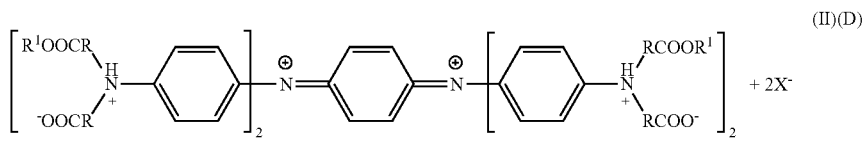

wherein X is preferably an anion of a strong acid and preferably comprises $NO_3^-$, tetrafluoroborate, hexafluorophosphate or hexafluoroantimonate. Most preferably, the acid comprises the salt of a strong acid. Preferred oxidants and oxidation conditions are the same as described above for the tris dyes. All of the compounds represented by these formulas (II)(A), (II)(B), (II)(C) and (II)(D) (and formulas (I)(A) and (I)(B) above) are stable, water-soluble near IR dyes and any of the above compounds may be blended with water-soluble polymers and lattices or latex emulsion polymers such as those enumerated herein to form IR absorbing compositions.

Thereafter, the oxidized dye may be further treated by reacting the ion X of the ionized dye compound with one or more counter-ions Y to form another salt of the dye, having the formula as shown for mono and di-oxidized dyes as illustrated in A and B below. Both the dyes are represented here as pure carboxylic acid salts but their zwitterions would behave similarly.

Monovalent dye salt:

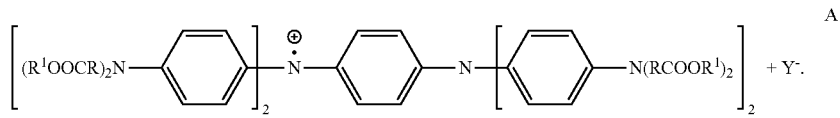

Divalent dye salt:

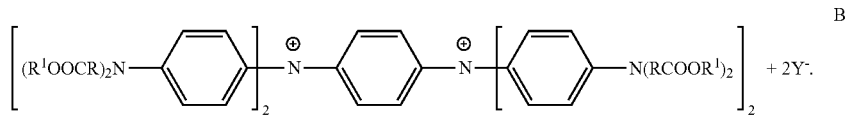

where Y is preferably $NO_3^-$, $SbF_6^-$, $BF_4^-$ or $PF_6^-$.

Similar to the tris dyes, this optional treatment adds a cation to the carboxylic acid, forming a neutrally charged species of the dye which is more stable and more easily isolated.

These stable, water-soluble near IR dyes have many of the same absorption properties described in earlier patents for near infrared dyes such as those claimed in U.S. Pat. Nos. 3,341,464, 3,440,257, 3,484,467, 3,575,871, 3,631,147, 3,637,769, 3,670,025 and 3,709,830. All of the dyes described in these patents absorb radiant energy in the near infrared portion of the spectrum, but they differ from the dyes of the present invention in that the present dyes are soluble in water and are environmentally safe to use.

The dyes of the invention may be blended with water-soluble polymers or lattices, or may be dissolved in aqueous solutions of water-soluble polymers, forming blend compositions. The blends may be coated onto a substrate or may be applied between two substrates, or may be extruded and/or molded into objects after partial or complete evaporation of water from the blends. Suitable water-soluble polymers are commercially available and well known in the art and non-exclusively include aqueous binders such as polyvinyl alcohol, silanol-modified polyvinyl alcohol, salts of partially hydrolyzed polyvinyl acetate, salts of hydrolyzed polyvinyl chloride-acetate copolymers, polysaccharide, starch, cationized starch, casein, gelatin, gelatin derivatives, cellulose and water-soluble cellulose derivatives such as water-soluble cellulose nitrate, water-soluble cellulose acetate, water-soluble cellulose propionate, water-soluble carboxymethyl cellulose, water-soluble hydroxyethyl cellulose, and water-soluble cellulose ethers such as ethyl and methyl cellulose polyvinylpyrrolidone, polyalkylene oxide and polyalkylene oxide derivative, aqueous acrylic resins and copolymers of acrylic acid, such as polyacrylic acid, methyl acrylate, methyl methacrylate, methylolacrylamide, polyacrylamide and copolymers thereof, aqueous alkyd resins, sulfonic acid salts of polystyrene and water-dispersible polymers such as aqueous latexes, including styrene butadiene latex, styrene-acryl latexes, and polyurethane latexes, and water-soluble emulsions, such as acryl emulsions. These aqueous binders can be used individually or in combination of two or more thereof. Of particular interest are those polymers such as cellulose acetate, propionate and natural products such as paper which have a natural affinity for water-soluble dyes.

When blended with aqueous solutions of water-soluble polymers, the dyes are preferably present in such the aqueous solution in an amount of from about 0.1% to about 10.0% by weight of the water plus the water-soluble polymer, preferably from about 4% to about 10% of the water plus the polymer, where the polymer comprises from about 30% to about 50% of the remainder with water comprising the balance. In most instances, parts or objects fabricated from these water-soluble polymers/dye formulations have a light path (thickness) from about 2 mils (50.8 μm) to about 20 mils (508 μm). However, there are applications in which it is desirable to use a very thin dye coating to block the near infrared portion of the spectrum. It is in that kind of application that the water-soluble dyes have special value. The thickness of the dye coating is usually less than about 0.1 mil (2.54 μm) to about 0.2 mil (5.08 μm). This requires dye concentrations in the polymer that are 10 to 100 times the concentration used in a solid plastic. The water-soluble dyes must be used in concentrations that are much greater than that accessible with most dyes formulated in plastic especially for so short a light path. Furthermore, a coating does not experience the thermal stress found in an injection molding operation. By using the water-soluble dye in an aqueous substrate, one is not constrained by concentration limits no matter how thin the coating.

In addition to being highly water soluble, the near infrared dye compositions have a greater thermal stability and greater water solubility than prior compositions. Accordingly, they are useful in a variety of applications. For example, when blended with a host polymer the dyes may be used to produce light-filtering or light-sensing elements or devices, such as optical filters including contact lenses, and filters for night vision devices, which may be fabricated by one of several conventional methods, such as injection molding. They are also useful as security inks. In formulation with available water-soluble stabilizers as well as other dyes, one may obtain tailored spectra meeting most application requirements. The dyes may include other additives or dyes to provide, for example, UV stabilization or a tailored spectral curve. The dye compositions also are useful in infrared elements in combination with other absorptive, reflective, refractive, or diffractive elements for optical radiation from the ultraviolet through the infrared.

The following examples serve to illustrate the invention:

EXAMPLE 1

Preparation of β-Alanine, N, N', N"-(nitrilotri-4,1-phenylene)tris[N-2 carboxyethyl]:

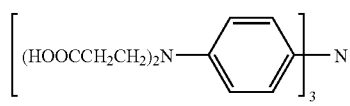

To 25 grams (0.086 mole) tris p-amino phenyl amine, is added 75 grams (1.04 mole) of acrylic acid. The exotherm from the addition rises the temperature to 40° C. to 45° C. Heating is continued with stirring at 50° C. for 2 to 2½ hours after which water (200 ml) is added. The precipitated solids are separated and washed repeatedly with water. The solids are collected on a filter and allowed to air dry. The solids weigh 45 grams, (70% of theory); melting pt.=165° C.- 168° C. Calculated for $C_{36}H_{42}N_4$ (based on atomic weights): C, 59.83; H, 5.82; N, 7.76 Found: C, 59.34; H, 5.77; N, 7.65

EXAMPLE 2

Ammonium salt of β-alanine, N, N', N"-(nitrilotri 4,1-phenylene) tris N-2 carboxyethyl—using weak base:

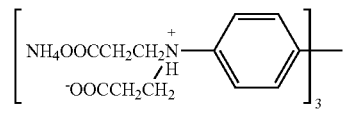

5.0 grams of the carboxylic acid from Example 1 was treated with 10 ml of concentrated ammonia in 50 ml of water. To this was added 200 ml of acetone which precipitated a dark green solid. The solid was washed on a filter with acetone and dried in vacuum. The analysis shows this to be a partially ammoniated salt of the carboxylic acid. Analysis for the mono ammonium salt is shown as follows:
Calculated for $C_{36}H_{51}N_7O_{12}$: C, 55.80; H, 6.60; N, 12.67
Found: C, 54.20; H, 7.30; N, 13.28

EXAMPLE 3

Sodium salt of β-alanine, N, N', N" nitrilotri 4,1-phenylene tris N-2-carboxylethyl using strong base:

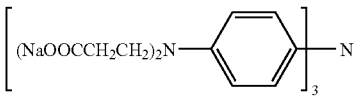

5.0 grams (0.0069 mole) of the carboxylic acid from example 1 was added to 20 ml of water. The slurry was stirred while adding 84 ml if 0.5 N NaOH (0.042 equiv). A solution forms which is filtered to remove any insolubles. To the filtered solution there is added 200 ml of acetone. A precipitate forms, washed with acetone and dried. Product weight: 6.1 g.
Calculated for $C_{36}H_{36}N_4O_{12}Na_6$: C, 50.58; H, 4.22; N, 6.56

EXAMPLE 4

Dye obtained by oxidation of the free acid β-alanine, N, N', N" nitrilotri 4,1-phenylene tris N-2-carboxylethyl

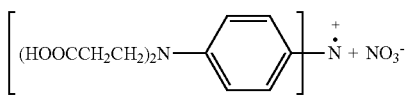

7.2 g (0.01 mole) of the parent carboxylic acid was dissolved in warm methanol. Filter the solution to remove any insolubles. Add 0.17 g (0.001 mole) of silver nitrate dissolved in a minimum amount of water. Heat the resulting mixture for 2 hours at 50° C. Filter off the silver precipitate with the addition of a celite filter aid (or another diatomaceous earth) and add 3 volumes of acetone to the methanol-water filtrate. Collect the solids that precipitate and wash them with acetone. Allow the solids to air dry. The yield, 6.0 g (76% of theory) had a λ max=954 nm, melting pt.=116° C.-120° C.

EXAMPLE 5

Dye obtained by oxidation of the ammonium salt of β-alanine, N, N', N" nitrilotri 4,1-phenylene tris N-2-carboxylethyl: using a weak base

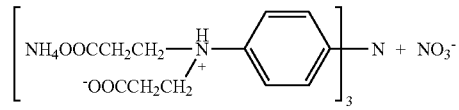

25.0 g (0.0866 mole) of tris p-aminophenyl amine was placed in a 500 ml flask to which was added 75 g (1.06 mole) of acrylic acid. The exotherm was complete when the temperature reaches 45° C. The mixture was heated with stirring for 2 hours at 50° C. At this point 25.0 g (0.08 mole) of concentrated ammonia was added and the reaction mixture was held at 50° C. for 30 minutes. Silver nitrate, 14.0 g (0.086 moles) was added in a minimum quantity of water and stirred for 2 hours at 50° C. The precipitated silver metal powder formed was removed by vacuum filtration using a filter aid such as celite. The filter cake was washed with three 25 ml portions of water. All filtrates were combined to which was added 1.5 liters of acetone. The solids that separate were allowed to settle and were recovered by decanting the acetone—water—acrylic acid mixture. The precipitated semi-solid was treated with 3×100 ml of acetone. The material collected was places in a vacuum dessicater over concentrated sulfuric acid and held under vacuum for 2 days. A glass—like solid was obtained. The solid was dissolved in warm methanol, filtered and the filtrate treated with 2x volume of acetone. A green solid separated and was collected on a filter, washed with acetone and air dried. The yield of product is 55 g (79% of theory). The dye has a λ max of 956 nm and absorptivity of 18.0.

EXAMPLE 6

Preparation of β-Alanine, N, N', N", N'''-[1,4-phenylenebis nitrilo-di-4,1-phenylene] tetrakis N-(2 carboxyethyl):

20 grams of N, N', N", N'''-tetrakis (p-aminophenyl)-p-phenylene-diamine is mixed with 48.8 g of acrylic acid to give a slurry. This mixture reacts spontaneously, increasing in temperatures to about 40° C. Continue to heat the stirred mixture at 50° C. for 2 to 3 hours. At the end of the reaction 200 ml of water was added to wash out the excess acrylic acid. The precipitated solids were removed by filtration and washed with water. The solids were allowed to air dry. The yield was 38.5 grams or 87% of theory; melting pt.=137° C.-138° C. Analysis gave the following results: Calculated for $C_{54}H_{60}O_{16}N_6$: C, 61.36; H, 6.44; N, 7.94 Found: C, 60.25; H, 5.86; N, 8.01

EXAMPLE 7

Sodium salt of β-Alanine N, N', N", N'''1,4-phenylene bis-nitrilo-di 4,1-phenylene] tetrakis N(2-carboxyethyl) using a weak base:

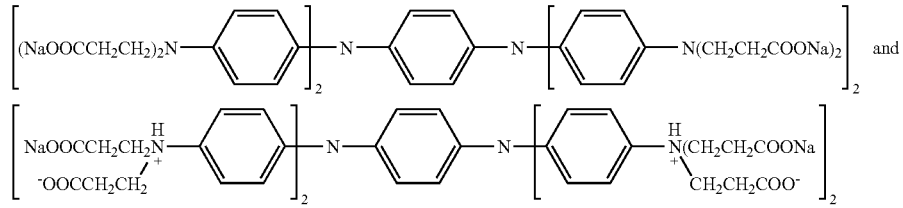

and

The above mixture was formed when 6.2 g (0.1 mole) of tetrakis parent amine is added to 57.6 g (0.8 mole) of acrylic acid. This mixture was heated at 50-60° C. for 4 hours with stirring. Add to the cooled solution over 1 hour 57.6 g (0.8 mole) of sodium bicarbonate dissolved in 100 ml of water. There was instantaneous gas evolution which gradually ceases during the addition. Addition of 400 ml of acetone gave a dark green precipitate. This was washed with acetone and dried in vacuum over concentrated $H_2SO_4$ as desiccant. A sample was subjected to analysis to give the following results:
Calculated for $C_{54}H_{56}O_{16}N_6Na_4$ (assuming the product is the zwitterion):
C, 57.04; H, 4.93; N, 7.39; Na, 8.09
Found: C, 53.01; H, 4.58; N, 6.71; Na, 12.10
Calculated for $C_{54}H_{52}O_{16}N_6Na_8$ (assuming the product is the fully neutralized salt):
C, 52.94; H, 4.25; N, 6.86; Na, 15.03
Found: C, 53.01; H, 4.58; N, 6.71; Na, 12.10

EXAMPLE 8

Dye from the sodium salt of β-Alanine N, N', N", N'''1,4-phenylene bis nitrilo-di 4,1-phenylene] tetrakis N(2 carboxyethyl) using a strong base: 10.0 g (0.0095 mole) of N, N', N", N''' tetrakis (p-amino phenyl)-p-phenylene diamine was neutralized with eight equivalents of 0.5 N sodium hydroxide (152.6 ml). To this solution there was added 3.244 g (0.019 mole) of silver nitrate in 10 cm³ of warm water. The solution darkened and was stirred while heating at 50° C. for 2½ hours. The precipitated silver was removed by filtration using filter aid such as celite. The filter cake was washed with 2×20 ml of water and the washings combined with the filtrate. To this dark solution there was added 3× the volume of acetone. A precipitate separated. It was allowed to settle and the supernatant was decanted. The solid was collected on a filter and was washed with 2×20 ml of acetone and allowed to air dry. The dye had a λ max in water of 1037 nm and an absorptivity of 18.0.

EXAMPLE 9

Dye from the sodium salt of β-Alanine N, N', N", N'''1,4-phenylene bis nitrilo-di 4,1-phenylene] tetrakis N(2 carboxyethyl) using a weak base: 10.48 g (0.01 mole) of N, N', N", N''' tetrakis (p-amino phenyl)-p-phenylene diamine was added to 90 ml of water. The slurry was stirred at room temperature as 6.72 g (0.08 mole) of sodium bicarbonate was added portion wise to the slurry. Gas evolution occurred with each addition but was easily controllable. When the addition was complete, a dark solution formed. To this solution, silver nitrate, 1.7g (0.01 mole), was added in 10 ml of warm water. The solution was stirred and held at 45° C. for 1.5 hours. The silver precipitate was removed by filtration in vacuum with the addition of filter aid such as celite. The dark aqueous filtrate was added to 350 ml of acetone. The solid that separated was washed with acetone. It was placed in a vacuum dessicator over conc. Sulfuric acid. The yield of solid was 11.5 g or 94% of theory; showed a color change at 203° C. but no melting up to 250° C. The spectrum of this dye in methanol had a λ max of 913 nm whereas a spectrum in water shows a peak absorption at 1030 nm.

EXAMPLE 10

Dye from the ammonium salt of β-Alanine N, N', N", N'''1,4-phenylene bis nitrilo-di 4,1-phenylene] tetrakis N(2 carboxyethyl) using a weak base: 31.6 g (0.03 mole) of N, N', N", N''' tetrakis (p-amino phenyl)-p-phenylene diamine was placed in a 500 ml beaker with a magnetic stirring bar. To this was added 14.6 g of concentrated (28%) ammonia in 75 ml of water. The solids went into solution. At this point 12.2 g of silver nitrate dissolved in 50 ml of warm water was added.

The solution darkened and was stirred at 50° C. After 1 hour an additional 14.6 g of concentrated ammonia was added and stirred at 50° C. for an additional hour. A celite filter aid was added to the solution to aid filtration by vacuum. The dark solution was then added to 500 ml of acetone. A precipitate formed which was isolated by decanting the supernatant liquid. The solids were washed with acetone to form a dark solid. The yield, 31 g is 83% of theory; melting pt.=156° C.-159° C. The spectrum of the product has a λ max at 950 nm.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A compound of the formula:

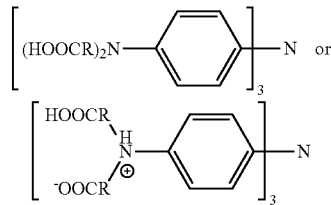

where R is dimethylene or where R has the formula $R^3CH_2CH_2$— and $R^3$ is methylene or a $C_2$ to $C_{10}$ polymethylene group of the formula —$(CH_2)_n$— where $2 \leq n \leq 10$.

2. A compound of claim 1 which has the formula:

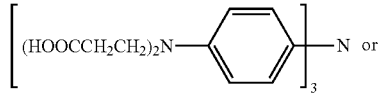

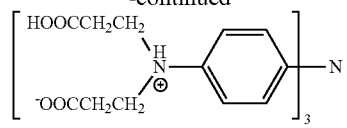

3. A salt produced from the compound of claim 1, the salt having the formula:

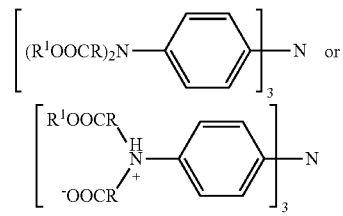

wherein $R^1$=Na$^+$, K$^+$, NH$_4^+$, (CH$_3$)$_4$N$^+$, (CH$_3$)$_3$NH$^+$, (R$^2$)$_3$NH$^+$ or R$^2$NH$_4^+$, and
$R^2$=CH$_3$(CH$_2$)$_n$, wherein n=2 to 10.

4. A dye produced from the salt of claim 3, the dye having the formula:

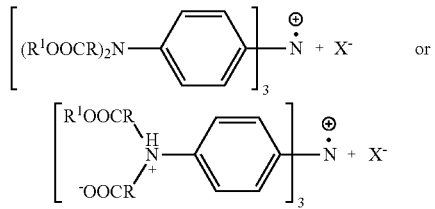

wherein X=NO$_3^-$, SbF$_6^-$, PF$_6^-$, BF$_4^-$, I$^-$, Cl$^-$, Br$^-$ or CH$_3$SO$_3^-$.

5. A water-soluble polymeric composition comprising a blend of the dye of claim 4 and a water-soluble polymer.

6. An aqueous composition comprising the dye of claim 4, a water-soluble polymer and water.

* * * * *